(12) United States Patent
Haberstich et al.

(10) Patent No.: US 9,782,215 B2
(45) Date of Patent: *Oct. 10, 2017

(54) SURGICAL INSTRUMENT WITH ULTRASONIC TRANSDUCER HAVING INTEGRAL SWITCHES

(71) Applicant: Ethicon Endo-Surgery, LLC, Guaynabo, PR (US)

(72) Inventors: Wells D. Haberstich, Loveland, OH (US); Kevin L. Houser, Springboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,530

(22) Filed: Jan. 28, 2016

(65) Prior Publication Data
US 2016/0206900 A1 Jul. 21, 2016

Related U.S. Application Data

(63) Continuation of application No. 13/274,516, filed on Oct. 17, 2011, now Pat. No. 9,247,986.
(Continued)

(51) Int. Cl.
*A61B 8/00* (2006.01)
*A61B 18/14* (2006.01)
(Continued)

(52) U.S. Cl.
CPC .... *A61B 18/1442* (2013.01); *A61B 17/00234* (2013.01); *A61B 17/2812* (2013.01);
(Continued)

(58) Field of Classification Search
CPC ...... A61N 7/00; H01M 2/1016; H01M 10/48; H01M 10/46; H02J 7/0047; H02J 7/0044;
(Continued)

(56) References Cited

U.S. PATENT DOCUMENTS 1,754,806 A 4/1930 Stevenson
3,297,192 A 1/1967 Swett
(Continued)

FOREIGN PATENT DOCUMENTS

DE 102008051866 10/2010
DE 102009013034 10/2010
(Continued)

OTHER PUBLICATIONS

Australian First Examination Report dated Jun. 11, 2015 for App. No. 2011323281.
(Continued)

*Primary Examiner* — Sanjay Cattungal
(74) *Attorney, Agent, or Firm* — Frost Brown Todd LLC

(57) ABSTRACT

An ultrasonic surgical device comprises a handle assembly, a shaft assembly, and a removable transducer module. The transducer module includes a waveguide, a locking mechanism, and an electronics assembly including at least one button. The handle assembly includes a trigger assembly configured to actuate the button(s) of the electronics assembly when the transducer module is coupled with the handle assembly. The shaft assembly engages the waveguide of the transducer module and is disposed at the distal end of the handle assembly. The distal end of the shaft assembly includes a harmonic blade. When assembled with the handle assembly, the transducer module is capable of providing ultrasonic energy to the harmonic blade.

20 Claims, 8 Drawing Sheets

Related U.S. Application Data

(60) Provisional application No. 61/487,846, filed on May 19, 2011, provisional application No. 61/410,603, filed on Nov. 5, 2010.

(51) Int. Cl.

| | |
|---|---|
| *H01M 2/26* | (2006.01) |
| *H01M 2/10* | (2006.01) |
| *A61B 18/12* | (2006.01) |
| *A61B 17/00* | (2006.01) |
| *A61B 17/32* | (2006.01) |
| *A61B 18/00* | (2006.01) |
| *A61B 18/04* | (2006.01) |
| *H02J 7/00* | (2006.01) |
| *A61B 17/28* | (2006.01) |
| *A61N 7/00* | (2006.01) |
| *A61B 34/00* | (2016.01) |
| *A61B 90/40* | (2016.01) |
| *A61B 46/10* | (2016.01) |
| *H01M 10/46* | (2006.01) |
| *H02J 7/02* | (2016.01) |
| *H01M 10/48* | (2006.01) |
| *A61B 90/00* | (2016.01) |
| *A61B 17/064* | (2006.01) |
| *A61B 17/285* | (2006.01) |
| *A61B 17/29* | (2006.01) |

(52) U.S. Cl.
CPC .......... *A61B 17/320068* (2013.01); *A61B 17/320092* (2013.01); *A61B 18/00* (2013.01); *A61B 18/04* (2013.01); *A61B 18/12* (2013.01); *A61B 18/1206* (2013.01); *A61B 18/14* (2013.01); *A61B 18/1445* (2013.01); *A61B 34/25* (2016.02); *A61B 46/10* (2016.02); *A61B 90/08* (2016.02); *A61B 90/40* (2016.02); *A61N 7/00* (2013.01); *H01M 2/10* (2013.01); *H01M 2/1016* (2013.01); *H01M 2/26* (2013.01); *H01M 10/46* (2013.01); *H01M 10/48* (2013.01); *H02J 7/0044* (2013.01); *H02J 7/0045* (2013.01); *H02J 7/0047* (2013.01); *H02J 7/025* (2013.01); *A61B 17/064* (2013.01); *A61B 17/285* (2013.01); *A61B 18/1233* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *H01M 2220/30* (2013.01); *H02J 2007/005* (2013.01); *Y10T 29/49005* (2015.01); *Y10T 29/49895* (2015.01); *Y10T 29/53913* (2015.01)

(58) Field of Classification Search
CPC .......... H02J 7/025; A61B 46/10; A61B 90/08; A61B 2017/00477; A61B 2017/00482; A61B 2018/00988; A61B 17/285; A61B 2018/1412; A61B 2018/1455; A61B 17/064; A61B 18/1233; A61B 2017/00084; A61B 2017/00398; A61B 2018/1226
USPC .................. 600/437–469; 601/1–3
See application file for complete search history.

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekumas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,871,493 A | 2/1999 | Sjostrom et al. |
| 5,873,873 A | 2/1999 | Smith et al. |
| 5,882,310 A | 3/1999 | Marian, Jr. |
| 5,893,835 A | 4/1999 | Witt et al. |
| 5,893,874 A | 4/1999 | Bourque et al. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |

(56) References Cited

U.S. PATENT DOCUMENTS

| | | |
|---|---|---|
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francishelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger et al. |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Her et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 * | 5/2010 | Shalton, IV ..... A61B 17/07207 227/176.1 |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 * | 7/2012 | Yates ............... A61B 17/07207 227/175.1 |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |

(56) References Cited

U.S. PATENT DOCUMENTS

| | | |
|---|---|---|
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,461,744 B2 | 6/2013 | Wiener et al. |
| 8,487,487 B2 | 7/2013 | Dietz et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,602,287 B2 | 12/2013 | Laurent et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanta et al. |
| 8,968,648 B2 | 3/2015 | Kaneko |
| 8,986,302 B2 | 3/2015 | Boudreaux et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,125 B2 | 6/2015 | Boudreaux |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,095,346 B2 | 8/2015 | Houser et al. |
| 9,113,903 B2 | 8/2015 | Unger et al. |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,421,062 B2 | 8/2016 | Houser et al. |
| 9,441,954 B2 | 9/2016 | Ramamurthy et al. |
| 9,500,472 B2 | 11/2016 | Ramamurthy et al. |
| 9,510,895 B2 | 12/2016 | Houser et al. |
| 9,526,921 B2 | 12/2016 | Kimball et al. |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1* | 3/2008 | Levy ................. A61C 1/00 433/118 |
| 2008/0147058 A1 | 6/2008 | Horrell et al. |
| 2008/0150754 A1 | 6/2008 | Quendt |
| 2008/0167670 A1* | 7/2008 | Shelton ........... A61B 17/07207 606/167 |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Joens et al. |
| 2009/0030437 A1* | 1/2009 | Houser ........ A61B 17/320092 606/169 |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0143798 A1* | 6/2009 | Smith ................ A61B 17/1285 606/169 |
| 2009/0143799 A1* | 6/2009 | Smith ................ A61B 17/1285 606/169 |
| 2009/0143800 A1 | 6/2009 | Deville et al. |
| 2009/0143801 A1* | 6/2009 | Deville ............. A61B 17/1285 606/169 |
| 2009/0143802 A1* | 6/2009 | Deville ............. A61B 17/1285 606/169 |
| 2009/0143803 A1* | 6/2009 | Palmer ............. A61B 17/1285 606/169 |
| 2009/0143804 A1* | 6/2009 | Palmer ............. A61B 17/1285 606/169 |
| 2009/0143805 A1* | 6/2009 | Palmer ........ A61B 17/320092 606/169 |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0076455 A1 | 3/2010 | Birkenbach et al. |
| 2010/0076474 A1* | 3/2010 | Yates ............. A61B 17/07207 606/170 |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1* | 12/2010 | Shelton, IV ........... A61B 17/00 227/175.4 |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |

(56) References Cited

U.S. PATENT DOCUMENTS

| | | | |
|---|---|---|---|
| 2011/0221398 A1 | 9/2011 | Ferber | |
| 2012/0111591 A1 | 5/2012 | Shelton, IV et al. | |
| 2012/0116260 A1 | 5/2012 | Johnson et al. | |
| 2012/0116261 A1 | 5/2012 | Mumaw et al. | |
| 2012/0116262 A1 | 5/2012 | Houser et al. | |
| 2012/0116263 A1 | 5/2012 | Houser et al. | |
| 2012/0116265 A1 | 5/2012 | Houser et al. | |
| 2012/0116266 A1 | 5/2012 | Houser et al. | |
| 2012/0116366 A1 | 5/2012 | Houser et al. | |
| 2012/0116380 A1 | 5/2012 | Madan et al. | |
| 2012/0116381 A1 | 5/2012 | Houser et al. | |
| 2012/0116391 A1 | 5/2012 | Houser et al. | |
| 2012/0179036 A1 | 7/2012 | Patrick et al. | |
| 2012/0265230 A1* | 10/2012 | Yates | A61B 17/07207 606/170 |
| 2012/0292367 A1* | 11/2012 | Morgan | A61B 17/072 227/175.1 |
| 2012/0305427 A1 | 12/2012 | Felder et al. | |
| 2013/0085330 A1 | 4/2013 | Ramamurthy et al. | |
| 2013/0090528 A1 | 4/2013 | Ramamurthy et al. | |
| 2013/0090675 A1 | 4/2013 | Mumaw et al. | |
| 2013/0118733 A1 | 5/2013 | Kumar | |
| 2014/0088379 A1 | 3/2014 | Bhamra et al. | |
| 2015/0305763 A1 | 10/2015 | Houser et al. | |
| 2016/0121143 A1 | 5/2016 | Mumaw et al. | |
| 2016/0329614 A1 | 11/2016 | Madan et al. | |
| 2016/0338760 A1 | 11/2016 | Houser et al. | |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H 10-118090 A | 5/1998 |
| JP | 2002-186627 A | 7/2002 |
| JP | 4602681 | 10/2005 |
| JP | 4836148 | 4/2010 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

Chinese First Office Action dated Apr. 16, 2016 for App. No. CN 201180063919X.
Chinese First Office Action dated Jun. 1, 2015 for App No. CN 2011800640981.
Japanese Office Action, Notification of Reasons for Refusal, dated Sep. 8, 2015 for App. No. 2013-537830.
Japanese Office Action, Notification of Reasons for Refusal, dated Aug. 25, 2015 for App. No. 2013-537831.
U.S. Office Action, Final, dated Apr. 1, 2015 for U.S. Appl. No. 13/151,481.
U.S. Office Action, Notice of Allowance, dated Feb. 25, 2015 for U.S. Appl. No. 13/151,509.
U.S. Office Action, Notice of Allowance, dated Feb. 17, 2015 for U.S. Appl. No. 13/151,512.
U.S. Office Action, Non-Final, dated Jan. 5, 2015 for U.S. Appl. No. 13/269,870.
U.S. Office Action, Final, dated Aug. 14, 2015 for U.S. Appl. No. 13/269,870.
U.S. Office Action, Notice of Allowance, dated Apr. 4, 2016 for U.S. Appl. No. 13/269,870.
U.S. Office Action, Notice of Allowance, dated Jul. 22, 2016 for U.S. Appl. No. 13/269,870.
U.S. Office Action, Final, dated Mar. 17, 2015 for U.S. Appl. No. 13/270,684.
U.S. Office Action, Notice of Allowance, dated Jul. 28, 2015 for U.S. Appl. No. 13/270,684.
U.S. Office Action, Notice of Allowance, dated Nov. 30, 2015 for U.S. Appl. No. 13/270,684.
U.S. Office Action, Non-Final, dated Mar. 26, 2015 for U.S. Appl. No. 13/271,352.
U.S. Office Action, Final, dated Jul. 15, 2015 for U.S. Appl. No. 13/271,352.
U.S. Office Action, Notice of Allowance, dated Feb. 19, 2016 for U.S. Appl. No. 13/271,352.
U.S. Office Action, Non-Final, dated Jul. 14, 2015 for U.S. Appl. No. 13/271,364.
U.S. Office Action, Notice of Allowance, dated Dec. 18, 2015 for U.S. Appl. No. 13/271,364.
U.S. Office Action, Notice of Allowance, dated Apr. 7, 2016 for U.S. Appl. No. 13/271,364.
U.S. Office Action, Non-Final, dated Apr. 2, 2015 for U.S. Appl. No. 13/274,496.
U.S. Office Action, Non-Final, dated Jul. 22, 2015 for U.S. Appl. No. 13/274,507.
U.S. Office Action, Final, dated Dec. 8, 2015 for U.S. Appl. No. 13/274,507.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 6, 2013 for U.S. Appl. No. 13/274,516.
U.S. Office Action, Final, dated Jun. 12, 2014 for U.S. Appl. No. 13/274,516.
U.S. Office Action, Non-Final, dated Oct. 8, 2014 for U.S. Appl. No. 13/274,516.
U.S. Office Action, Final, dated May 8, 2015 for U.S. Appl. No. 13/274,516.
U.S. Office Action, Notice of Allowance, dated Sep. 24, 2015 for U.S. Appl. No. 13/274,516.
U.S. Office Action, Notice of Allowance, dated Jan. 21, 2015 for U.S. Appl. No. 13/274,540.

(56) References Cited

OTHER PUBLICATIONS

U.S. Office Action, Notice of Allowance, dated Jan. 21, 2015 for U.S. Appl. No. 13/274,805.
U.S. Office Action, Notice of Allowance, dated Mar. 23, 2015 for U.S. Appl. No. 13/274,830.
U.S. Office Action, Non-Final, dated Feb. 25, 2015 for U.S. Appl. No. 13/275,495.
U.S. Office Action, Final, dated Mar. 10, 2015 for U.S. Appl. No. 13/275,547.
U.S. Office Action, Final, dated Mar. 13, 2015 for U.S. Appl. No. 13/276,673.
U.S. Office Action, Notice of Allowance, dated Dec. 23, 2014 for U.S. Appl. No. 13/276,687.
U.S. Office Action, Non-Final, dated Jan. 29, 2015 for U.S. Appl. No. 13/276,707.
U.S. Office Action, Notice of Allowance, dated Mar. 13, 2015 for U.S. Appl. No. 13/276,725.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
EP Communication dated Feb. 19, 2014 for Application No. EP 11781972.2.
International Search Report and Written Opinion dated Jan. 26, 2012 for Application No. PCT/US2011/059212.
International Preliminary Report on Patentability dated May 7, 2013 for Application No. PCT/US2011/059212.
Communication from International Searching Authority dated Jan. 24, 2012 for Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.
International Search Report dated Feb. 13, 2012 for Application No. PCT/US2011/059217.
International Preliminary Report on Patentability dated May 7, 2013 for Application No. PCT/US2011/059217.
International Search Report dated Jun. 12, 2012 for Application No. PCT/US2011/059218.
International Preliminary Report on Patentability dated May 7, 2013 for Application No. PCT/US2011/059218.
International Search Report dated Jan. 26, 2012 for Application No. PCT/US11/059220.
International Preliminary Report on Patentability dated May 7, 2013 for Application No. PCT/US2011/059220.
Communication from International Searching Authority dated Feb. 2, 2012 for Application No. PCT/US2011/059222.
International Search Report dated Apr. 18, 2012 for Application No. PCT/US2011/059222.
International Preliminary Report on Patentability dated May 7, 2013 for Application No. PCT/US2011/059222.
International Search Report dated Feb. 1, 2012 for Application No. PCT/US11/059223.
International Preliminary Report on Patentability dated May 7, 2013 for Application No. PCT/US2011/059223.
International Search Report dated Jan. 12, 2012 for Application No. PCT/US11/059226.
International Preliminary Report on Patentability dated May 7, 2013 for Application No. PCT/US2011/059226.
International Search Report dated Mar. 15, 2012 for Application No. PCT/US2011/059338.
International Search Report dated Feb. 7, 2012 for Application No. PCT/US2011/059351.
International Preliminary Report on Patentability dated May 7, 2013 for Application No. PCT/US2011/059351.
International Search Report dated Feb. 2, 2012 for Application No. PCT/US2011/059354.
International Preliminary Report on Patentability dated May 7, 2013 for Application No. PCT/US2011/059354.
International Search Report dated May 29, 2012 for Application No. PCT/US11/059358.
International Preliminary Report on Patentability dated May 7, 2013 for Application No. PCT/US2011/059358.
Communication from International Searching Authority dated Feb. 6, 2012 for Application No. PCT/US2011/059362.
International Search Report dated Mar. 22, 2012 for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from International Searching Authority dated Feb. 2, 2012 for Application No. PCT/US2011/059378.
International Search Report dated May 24, 2012 for Application No. PCT/US2011/059378.
International Search Report and Written Opinion dated Feb. 2, 2012 for Application No. PCT/US2011/059378.
International Preliminary Report on Patentability dated May 7, 2013 for Application No. PCT/US2011/059378.
International Search Report dated Apr. 11, 2012 for Application No. PCT/US2011/059381.
International Search Report and Written Opinion dated Jul. 6, 2012 for PCT/US2011/059381.
International Preliminary Report on Patentability dated May 8, 2013 for Application No. PCT/US2011/059381.
Office Action Non-Final dated Aug. 6, 2013 for U.S. Appl. No. 13/151,471.
Notice of Allowance dated Dec. 6, 2013 for U.S. Appl. No. 13/151,471.
Office Action Non-Final dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
U.S. Office Action, Non-Final, dated Aug. 14, 2014 for U.S. Appl. No. 13/151,481.
Restriction Requirement dated Jul. 5, 2013 for U.S. Appl. No. 13/151,488.
U.S. Office Action, Non-Final, dated Nov. 7, 2014 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Office Action Non Final dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
Office Action Non Final dated Jun. 18, 2014 for U.S. Appl. No. 13/151,503.
Office Action Non Final dated Nov. 6, 2014 for U.S. Appl. No. 13/151,503.

(56) References Cited

OTHER PUBLICATIONS

Restriction Requirement dated Mar. 13, 2013 for U.S. Appl. No. 13/151,509.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Jan. 29, 2014 for U.S. Appl. No. 13/151,509.
Office Action Non-Final dated Jul. 9, 2014 for U.S. Appl. No. 13/151,509.
U.S. Office Action, Notice of Allowance, dated Oct. 28, 2014 for U.S. Appl. No. 13/151,509.
Restriction Requirement dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Restriction Requirement, dated Jul. 11, 2014 for U.S. Appl. No. 13/269,870.
Restriction Requirement dated Feb. 28, 2013 for U.S. Appl. No. 13/270,667.
Office Action Non-Final dated Apr. 26, 2013 for U.S. Appl. No. 13/270,667.
Office Action Final dated Oct. 25, 2013 for U.S. Appl. No. 13/270,667.
U.S. Office Action, Non-Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Restriction Requirement, dated Sep. 11, 2014 for U.S. Appl. No. 13/270,701.
U.S. Office Action, Non-Final, dated Dec. 16, 2014 for U.S. Appl. No. 13/270,701.
Office Action Non-Final dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Restriction Requirement, dated Oct. 2, 2013 for U.S. Appl. No. 13/274,480.
Office Action Non-Final dated Feb. 14, 2014 for U.S. Appl. No. 13/274,480.
U.S. Office Action, Final, dated Jul. 17, 2014 for U.S. Appl. No. 13/274,480.
U.S. Office Action, Restriction Requirement, dated Dec. 9, 2013 for U.S. Appl. No. 13/274,496.
U.S. Office Action, Non-Final, dated Feb. 6, 2014 for U.S. Appl. No. 13/274,496.
U.S. Office Action, Final, dated May 15, 2014 for U.S. Appl. No. 13/274,496.
U.S. Office Action, Final, dated Aug. 22, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Restriction Requirement dated Feb. 25, 2013 for U.S. Appl. No. 13/274,540.
Office Action Non-Final dated Apr. 30, 2013 for U.S. Appl. No. 13/274,540.
Office Action Final dated Oct. 25, 2013 for U.S. Appl. No. 13/274,540.
U.S. Office Action, Non-Final, dated Aug. 26, 2014 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
U.S. Office Action, Non-Final, dated Aug. 14, 2014 for U.S. Appl. No. 13/274,805.
U.S. Office Action, Notice of Allowance, dated Nov. 28, 2014 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Office Action Final dated Nov. 26, 2013 for U.S. Appl. No. 13/274,830.
U.S. Office Action, Non-Final, dated Oct. 22, 2014 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Final dated Dec. 5, 2013 for U.S. Appl. No. 13/275,495.
Office Action Non-Final dated Jan. 6, 2014 for U.S. Appl. No. 13/275,514.
U.S. Office Action, Non-Final, dated Sep. 9, 2014 for U.S. Appl. No. 13/275,514.
Office Action Non-Final dated May 17, 2013 for U.S. Appl. No. 13/275,547.
Office Action Final dated Feb. 28, 2014 for U.S. Appl. No. 13/275,547.
U.S. Office Action, Non-Final, dated Aug. 20, 2014 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
U.S. Office Action, Non-Final, dated Oct. 23, 2014 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
U.S. Office Action, Restriction Requirement, dated Jul. 9, 2014 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Office Action Final dated Mar. 21, 2014 for U.S. Appl. No. 13/276,673.
U.S. Office Action, Non-Final, dated Aug. 14, 2014 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Notice of Allowance dated Nov. 12, 2013 for U.S. Appl. No. 13/276,687.
Notice of Allowance dated Jun. 2, 2014 for U.S. Appl. No. 13/276,687.
U.S. Office Action, Notice of Allowance, dated Sep. 12, 2014 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Office Action Final dated Sep. 27, 2013 for U.S. Appl. No. 13/276,707.
Restriction Requirement dated Feb. 6, 2013 for U.S. Appl. No. 13/276,725.
U.S. Office Action, Non-Final, dated Aug. 20, 2014 for U.S. Appl. No. 13/276,725.
Restriction Requirement dated Dec. 21, 2012 for U.S. Appl. No. 13/276,745.

(56) References Cited

OTHER PUBLICATIONS

Office Action Non-Final dated Apr. 30, 2013 for U.S. Appl. No. 13/276,745.
Office Action Final dated Nov. 8, 2013 for U.S. Appl. No. 13/276,745.
Office Action Non-Final dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Restriction Requirement, dated Sep. 24, 2014 for U.S. Appl. No. 13/277,328.
U.S. Office Action, Non-Final, dated Dec. 8, 2014 for U.S. Appl. No. 13/277,328.

* cited by examiner

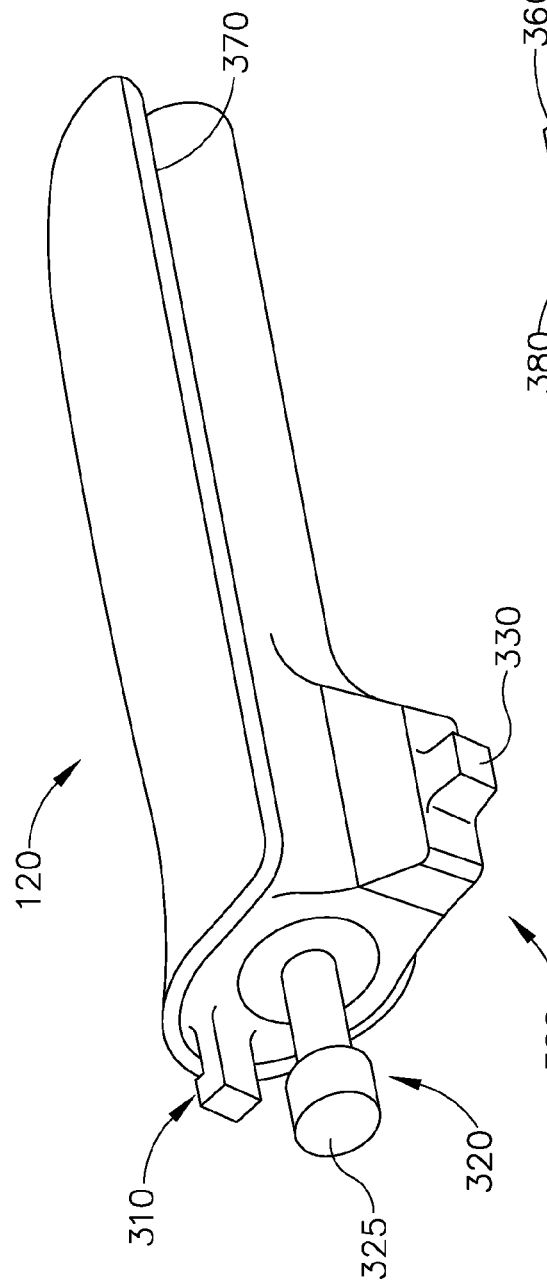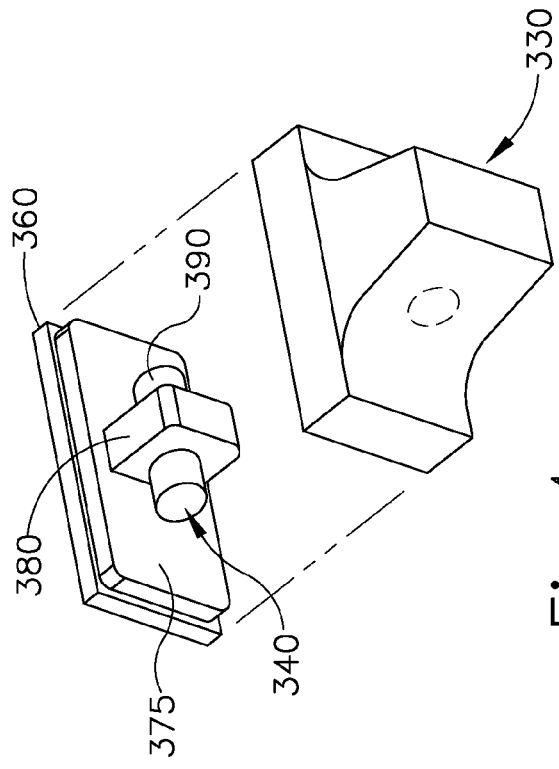

SURGICAL INSTRUMENT WITH ULTRASONIC TRANSDUCER HAVING INTEGRAL SWITCHES

PRIORITY

This application is a continuation of U.S. application Ser. No. 13/274,516, filed Oct. 17, 2011, entitled "Surgical Instrument with Ultrasonic Transducer Having Integral Switches," now U.S. Pat. No. 9,247,986, issued Feb. 2, 2016, which claims priority to U.S. Provisional Application Ser. No. 61/410,603, filed Nov. 5, 2010, entitled "Energy-Based Surgical Instruments," the disclosure of which is incorporated by reference herein.

U.S. application Ser. No. 13/274,516 also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,174, issued Feb. 25, 2014, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. It should be understood that the devices described in the above-cited references may be readily adapted to include an integral power source, such as those described herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Additional exemplary surgical instruments are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, now U.S. Pat. No. 9,161,803, issued Oct. 20, 2015, the disclosure of which is incorporated by reference herein. The devices described in those references may also be readily adapted to include an integral power source, such as those described herein.

As described in greater detail below, surgical instruments may be constructed with modular parts such that parts can be readily replaced or otherwise changed by a user. For instance, such modularity may enable selection of different end effectors for different settings, different shaft lengths, different operating modalities, etc. In addition or in the alternative, replaceability may provide a dichotomy of reusable and disposable parts of a surgical instrument. For instance, a surgical instrument may have a reusable handle assembly with a disposable shaft and end effector.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a perspective view of the removable transducer module of the surgical device of FIG. 1;

FIG. 4 depicts a partial view of an electronics module and overmolded boot of the removable transducer module of FIG. 3;

Figure 1:
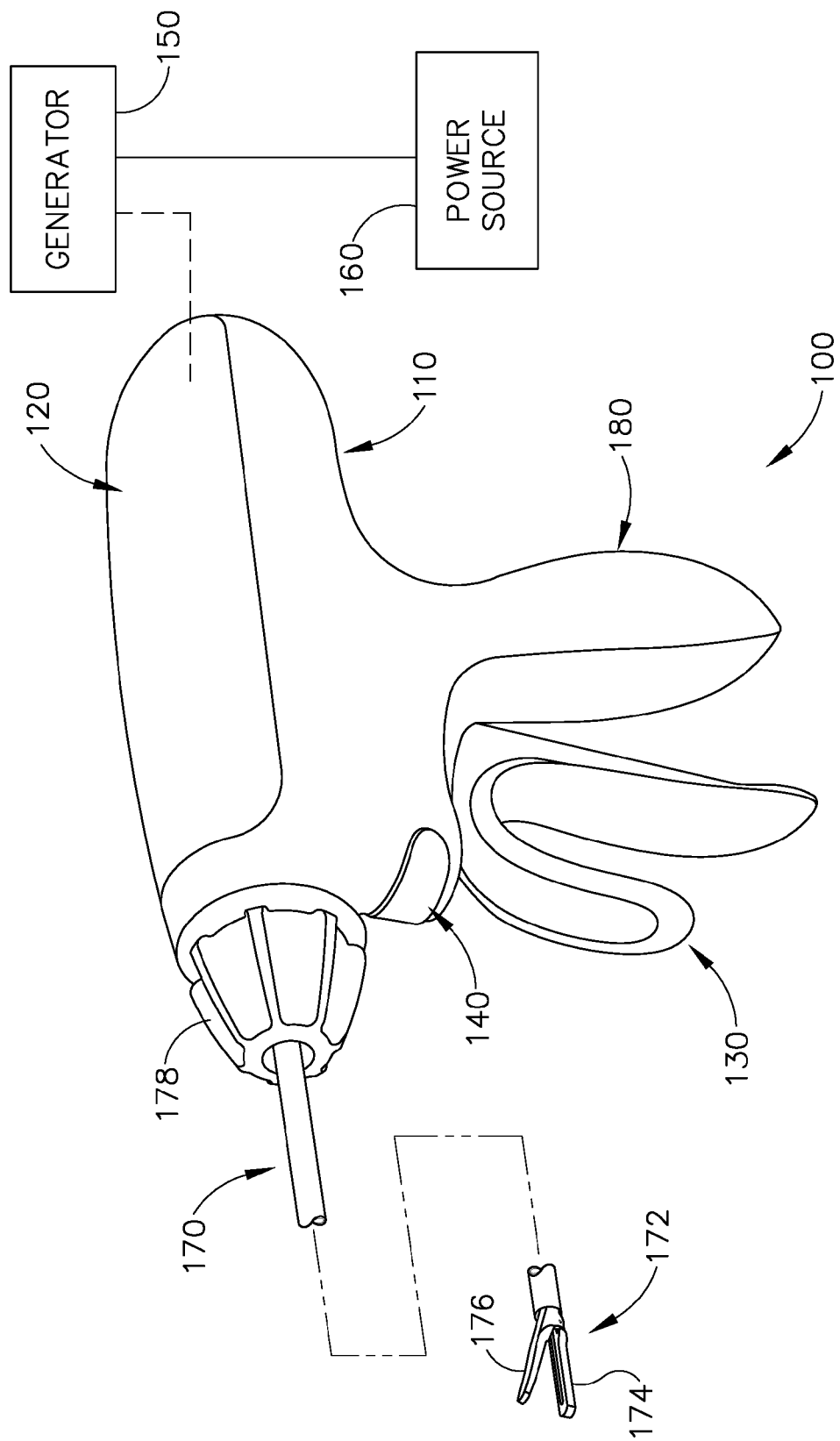
FIG. 1 depicts a perspective view of an exemplary surgical device having a removable transducer module.

The drawings are not intended to be limiting in any way, and it is contemplated that various versions of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, versions, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

FIG. 1 shows an exemplary ultrasonic surgical device (100) comprising a handle (110) and a removable ultrasonic transducer module (120). Handle (110) further comprises a trigger assembly (130), a toggle button (140), a shaft assembly (170), and a grip (180). In the present example, surgical device (100) is coupled with a generator (150), which is in turn coupled with a power source (160). By way of example only, surgical device (100) and generator (150) may be provided and coupled in accordance with the teachings of U.S. Patent App. Publ. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should be understood, however, that a generator and/or other type of power source may be integrally provided within transducer module (120) and/or within handle (110). Merely illustrative examples of how a power source may be integrated into a surgical instrument are disclosed in one or more of the references cited herein.

Any portion of ultrasonic surgical device (100) may be readily modified in accordance with the teachings of any of the references cited herein. For instance, in addition to or as an alternative to operating on tissue using ultrasonic energy, surgical device (100) may comprise an RF electrosurgical device, a powered endocutter type of device, a clip applier, and/or any other suitable type of device. It should therefore be understood that the teachings herein are not limited to ultrasonic instruments. By way of example only, surgical device (100) may be constructed in accordance with at least some of the teachings of U.S. Pat. Nos. 5,980,510; 6,500,176; 6,783,524; 7,112,201; 7,125,409; 7,169,146; 7,186,253; 7,189,233; 7,220,951; 7,309,849; 7,311,709; 7,354,440; 7,381,209; 7,416,101; 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0143797, now U.S. Pat. No. 8,419,757; U.S. Pub. No. 2009/0209990, now U.S. Pat. No. 8,657,174; U.S. Pub. No. 2010/0069940, now U.S. Pat. No. 9,023,071; U.S. Pub. No. 2011/0015660, now U.S. Pat. No. 8,461,744; U.S. Pat. Pub. No. 2011/0087218, now U.S. Pat. No. 8,939,974; U.S. patent application Ser. No. 13/151,481, now U.S. Pat. No. 9,161,803; and/or U.S. Provisional Application Ser. No. 61/410,603. The disclosures of each of those documents are incorporated by reference herein in their entirety.

In the present example, transducer module (120) may be detachably installed together with handle (110) to form a substantially flush and uninterrupted surface. Handle (110) and transducer module (120) together form a single surgical device (100) operable to deliver ultrasonic energy through shaft assembly (170). Shaft assembly (170) also includes a distally positioned end effector (172), which includes a harmonic blade (174) and pivotable clamp member (176). A knob (178) is operable to rotate the entire shaft assembly (170) relative to handle (110), such as to advantageously position end effector (172) at a surgical site, etc. While harmonic blade (174) is substantially straight in the present example, it should be understood that harmonic blade (174) may alternatively be curved and/or have any other suitable configuration. It should also be understood that pivotable clamp member (176) is merely optional. By way of example only, end effector (172) may be constructed and operable in accordance with the teachings of any of the reference cited herein; and/or in any other suitable fashion. A waveguide (not shown) extends internally along the length of shaft assembly (170) and is configured to transmit ultrasonic vibrations from transducer module (120) to harmonic blade (174) when shaft assembly (170) is coupled with transducer module (120) as described in greater detail below.

It should be understood that handles (110) with different kinds of end effectors (172) may be selected and coupled with transducer module (120) depending on the setting and desired use. Additionally, by providing a detachable transducer module (120), it may be possible to reduce the downtime between uses by enabling transducer module (120) to be installed into and used with a second handle (110) while a first handle (110) is being sterilized, serviced, recycled, disposed of, etc. Any portion of ultrasonic surgical device (100) may be readily modified in accordance with the teachings of any of the references cited herein. As noted above, in addition to or as an alternative to having a harmonic blade (174), surgical device (100) may comprise an RF electrosurgical device, a powered endocutter type of device, a clip applier, and/or any other suitable type of device. In some instances, transducer module (120) is replaced with a motor, a generator, some other type of power source, a control module, etc., depending on the type of end effector being used. The same handle (110) may accommodate the various kinds of shaft assemblies, end effectors, and replacements for transducer module (120).

Figure 2:
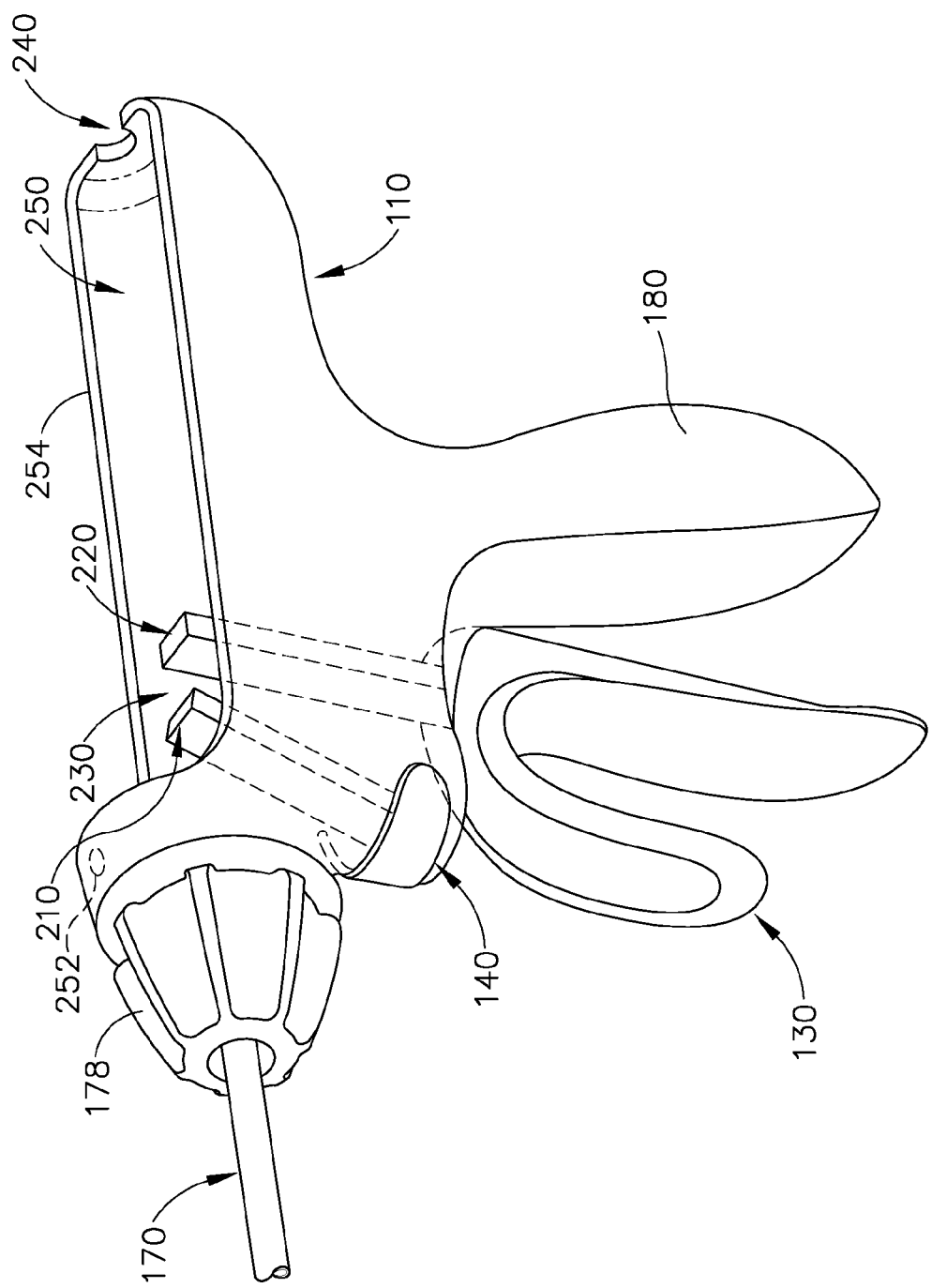
FIG. 2 depicts a perspective view of the surgical device of FIG. 1, with the transducer module removed.

FIG. 2 shows handle (110) of surgical device (100) with transducer module (120) removed. In the present example, an upper portion of handle (110) defines an opening and cavity (250) for accommodating and encompassing at least a portion of transducer module (120). It should be understood that cavity (250) is defined by side portions and a proximal portion of handle (110) in the present example, though cavity (250) may instead simply be defined by side portions and/or otherwise be defined. As another merely illustrative example, handle (110) may be configured to receive transducer module (120) along a lateral insertion path and/or a distally directed longitudinal insertion path instead of along a vertically downward insertion path. Other suitable ways in which handle (110) may receive and accommodate transducer module (120) will be apparent to those of ordinary skill in the art in view of the teachings herein.

In the present example, the upper portion of the handle (110) further comprises a recess (252) for receiving a tab hook (310) of transducer module (120) and thereby securing transducer module (120) to handle (110) as will be described in greater detail below. In some versions, a plurality of tab hooks and recesses may be provided. The proximal portion of handle (110) may also include one or more features to selectively retain the proximal end of transducer module (120). By way of example only, handle (110) and transducer module (120) may be secured together with one or more fastening features such as clasps, latches, clips, clamps, straps, locks, snap-fittings, thumb screws, push-push quick release fasteners, push-turn quick release fasteners, etc. Other suitable ways in which transducer module (120) may be releasably secured to handle (110) will be apparent to those of ordinary skill in the art in view of the teachings herein.

Figure 5:
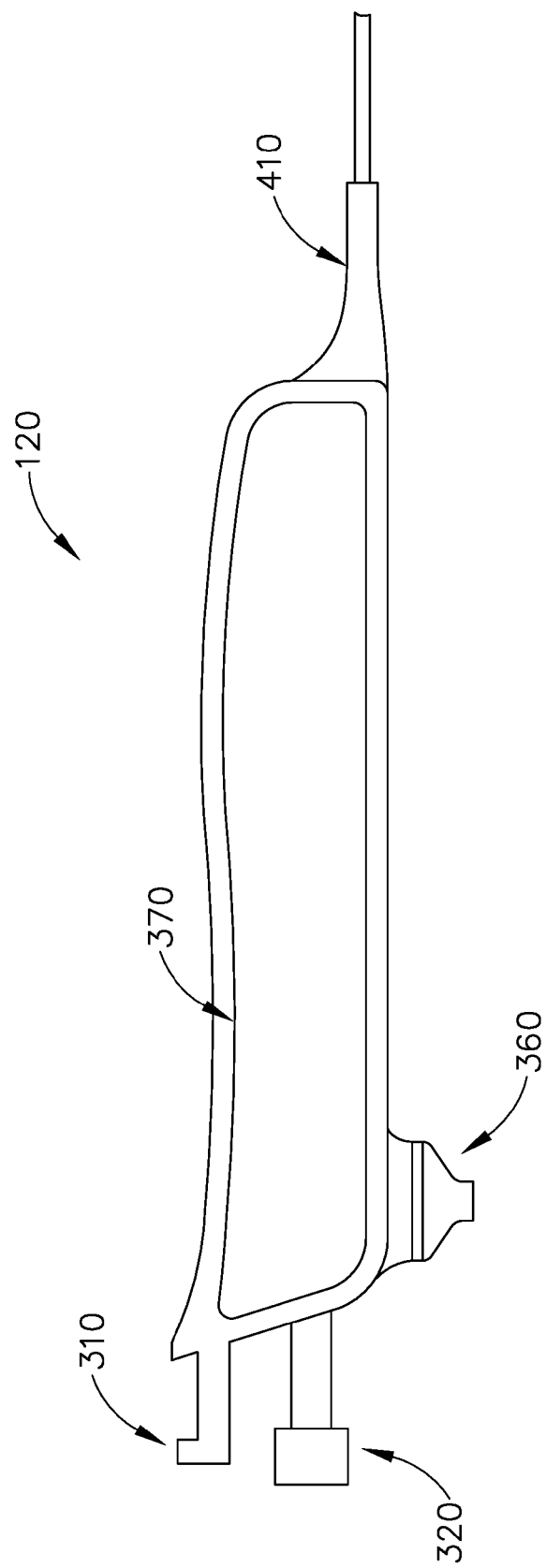
FIG. 5 depicts a side elevation view of the removable transducer module of FIG. 3, with a cable.

In some versions where an external power source (160) and/or an external generator (150) are provided, and as shown in FIG. 2, a recessed edge (240) is included in handle (110) to accommodate cables or other connections. For instance, as shown in FIG. 5, such a cable (410) may be integral with transducer module (120) or be otherwise coupled with transducer module (120), and may extend proximally from transducer module (120). Cable (410) of this example couples transducer module (120) with external components such as generator (150). Recessed edge (240) of handle (110) is configured to accommodate cable (410) when transducer module (120) is coupled with handle (110).

In the present example, trigger assembly (130) is pivotable relative to grip (180) of handle (110). Trigger assembly (130) further comprises a mechanical lever end (220) operable to pivot in conjunction with the trigger assembly (130). The handle (110) is further provided with a toggle button (140) including a mechanical lever end (210). Lever ends (210, 220) are disposed opposite of one another to form a gap (230). When trigger assembly (130) and toggle button (140) are actuated, mechanical lever end (220) and mechanical lever end (210) are operable to correspondingly move toward and away from one another. In particular, one of the trigger assembly (130) and the toggle button (140) may be actuated to selectively activate the ultrasonic surgical device (100) while the other one of the trigger assembly (130) and the toggle button (140) may be actuated to toggle between a maximum and a minimum power level, as will be described in greater detail below.

Figure 7:
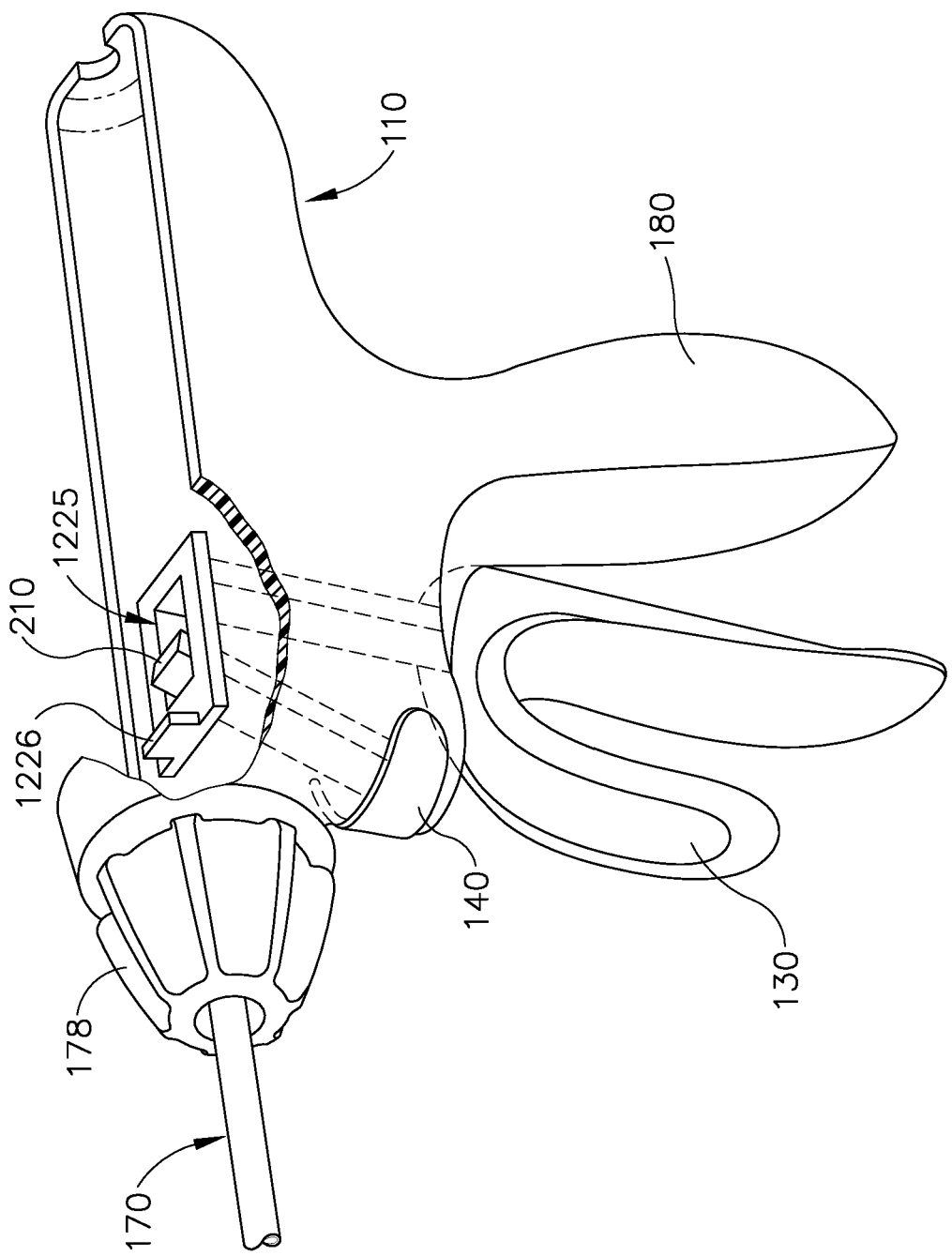
FIG. 7 depicts an exemplary alternative handle assembly, including a clamp actuating tab.
Figure 8:
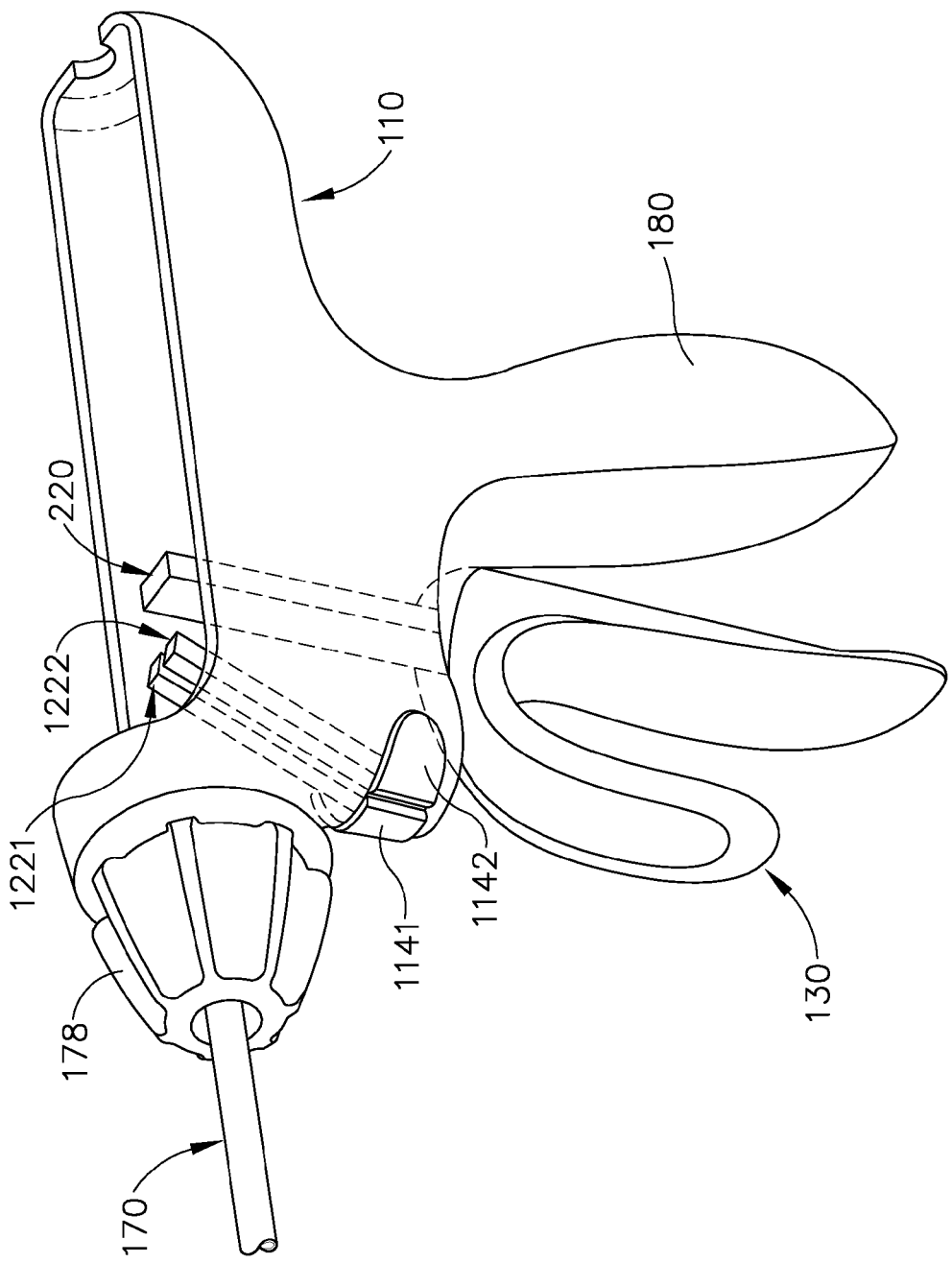
FIG. 8 depicts another exemplary alternative handle assembly, including a pair of toggle buttons.
Figure 9:
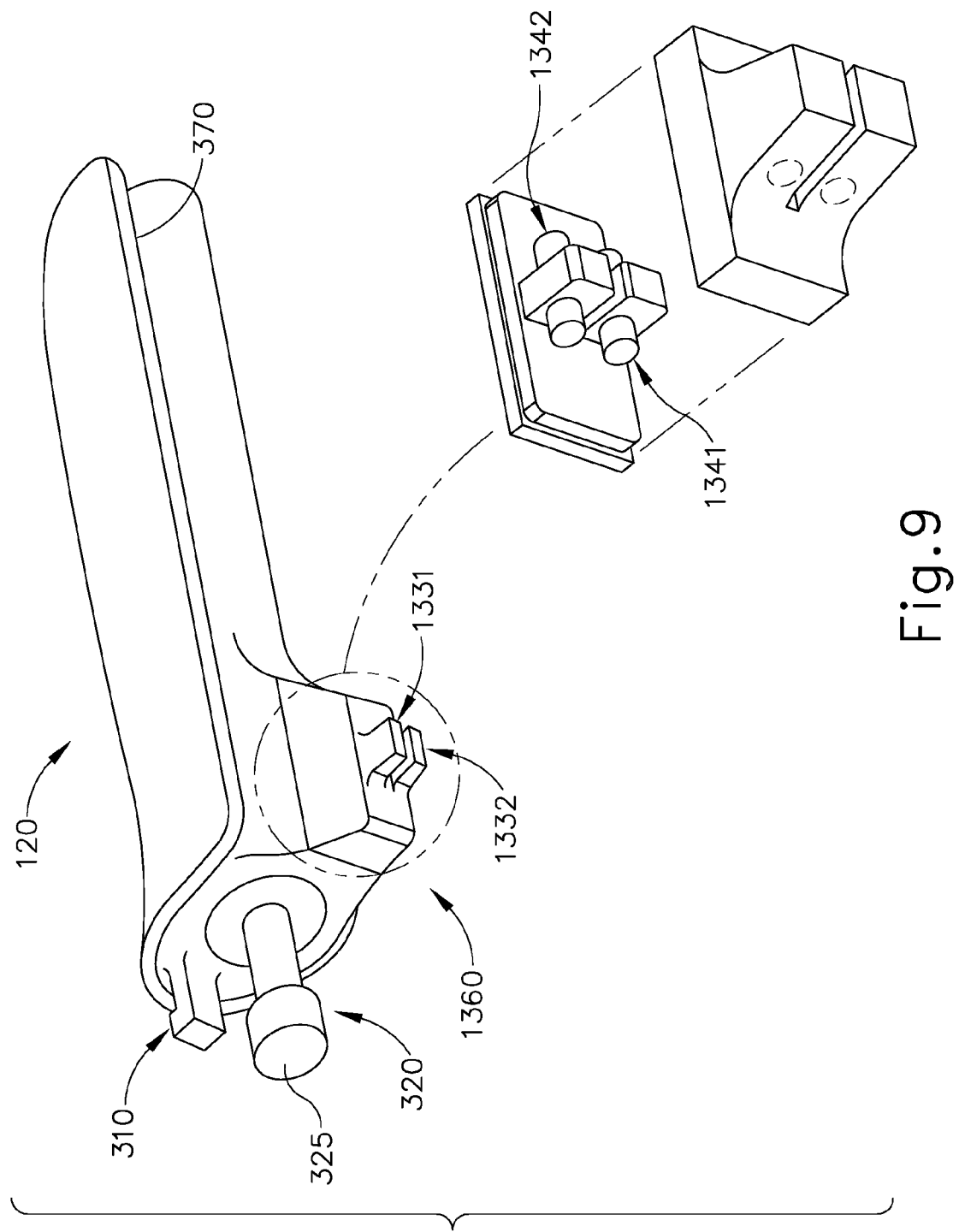
FIG. 9 depicts an exemplary alternative transducer module, including a pair of forward facing buttons.

In the present example, toggle button (140) may be actuated to select a power level. For instance, repeatedly pressing toggle button (140) may cycle through a set of predefined power levels. Closure of trigger assembly (130) with toggle button (140) depressed causes substantially simultaneous closure of end effector (172) and activation of blade (174) at the selected power level. In some other versions, trigger assembly (130) only pivots clamp member (176) toward blade (174); while toggle button (140) only activates blade (174). FIG. 7 shows an example of a clamp actuating tab (1226) that is driven by trigger assembly (130) and that communicates with clamp member (176). For instance, clamp actuating tab (1226) may engage a force limiting mechanism (not shown) that communicates with an inner tubular actuating member (not shown) that extends through shaft assembly (170) and that is pivotally coupled with clamp member (176). Examples of such assemblies are described in various references that are cited herein. The version shown in FIG. 7 includes a recess (1225) that is configured to receive electronics module (360) as described elsewhere herein. As yet another merely illustrative example, as shown in FIG. 8, a pair of toggle buttons (1141, 1142) may be provided for independent actuation of two corresponding lever ends (1221, 1222). Lever ends (1221, 1222) may selectively activate corresponding buttons (1341, 1342) of the exemplary alternative electronics module (1360) shown in FIG. 9. As also shown, buttons (1341, 1342) may include their own respective boots (1331, 1332).

FIGS. 3-5 show transducer module (120) in greater detail. Transducer module (120) includes integral tab hook (310) for engaging with handle (110) of surgical device (100) as noted above. Transducer module (120) further includes a distally extending waveguide (320). Waveguide (320) is in acoustic communication with piezoelectric elements (not shown) that are within transducer module (120) and that are configured to convert electrical power into ultrasonic vibrations. Waveguide (320) is acoustically coupled with a corresponding waveguide of shaft assembly (170) when transducer module (120) is fully seated in handle (110), to transmit ultrasonic vibrations from transducer module (110) to end effector (172). Thus, when tissue is secured between blade (174) and pivoting member (176), the ultrasonic oscillation of blade (174) may simultaneously sever the tissue and denature the proteins in adjacent tissue cells, thereby providing a coagulative effect with relatively little thermal spread. An electrical current may also be provided through blade (174) and pivoting member (176) to also cauterize the tissue.

In the present example, waveguide (320) includes a head portion (325) for coupling with the corresponding receiving portion of the waveguide of shaft assembly (170). For instance, such a head portion (325) and corresponding receiving portion may provide sufficient acoustic continuity without requiring any component of shaft assembly (170) to be screwed onto waveguide (320). By way of example only, the waveguide of shaft assembly (170) may couple with the waveguide (320) of transducer module (120) in accordance with the teachings of U.S. Pub. No. 2007/0129723, entitled "Ultrasonic Medical Instrument and Medical Instrument Connection Assembly," published Jun. 7, 2007, now U.S. Pat. No. 8,246,642, issued Aug. 21, 2012, the disclosure of which is incorporated by reference herein; U.S. Pat. No. 6,561,983, entitled "Attachments of Components of Ultrasonic Blades or Waveguides," issued, May 23, 2003, the disclosure of which is incorporated by reference herein; and/or U.S. Pat. No. 6,051,010, entitled "Methods and Devices for Joining Transmission Components," issued, Apr. 18, 2000, the disclosure of which is incorporated by reference herein.

In some other versions, the receiving portion of the waveguide of shaft assembly (170) may include internal threads that complement external threads on head portion (325), such that the waveguide of shaft assembly (170) must be rotated to fully couple with head portion (325) after transducer module (120) is seated in handle (110). A torque wrench (not shown) may be provided to ensure that the proper amount of torque is used for such a coupling. Alternatively, the user may simply tighten by hand. It should also be understood that, regardless of how blade (174) is coupled with transducer module (120), a transducer within transducer module (120) may rotate within transducer module (120) and relative to handle (110). End effector (172) may rotate with the transducer (e.g. to optimally orient end effector (172) within the patient). In versions where the transducer rotates within transducer module (120) and where the waveguide of shaft assembly (170) threadably couples with the transducer, a pin and/or other feature (e.g., solenoid, etc.) may be used to selectively prevent rotation of the transducer within transducer module (120) while the waveguide of shaft assembly (170) is being coupled with the transducer. Various suitable ways in which the rotation of the transducer may be selectively restricted will be apparent to those of ordinary skill in the art in view of the teachings herein. Similarly, other suitable ways in which harmonic blade (174) may be acoustically coupled with transducer module (120) will be apparent to those of ordinary skill in the art in view of the teachings herein.

Transducer module (120) of the present example further comprises an electronics module (360). Electronics module (360) is located on an underside of transducer module (120) and may be installed into the cavity (250) of the handle (110). In particular, electronics module (360) is positioned to be located in gap (230) between lever ends (210, 220) when transducer module (120) is seated in handle (110). Electronics module (360) includes a base member (375) presenting a switch assembly (380). Switch assembly (380) includes a first button (340) and a second button (390). Switch assembly (380) may employ various types of switches, including but not limited to: contact, pressure, capacitance, push-button, rocker, thin film, etc. Of course, the types and positioning of the switches may take any other suitable forms.

During installation of transducer module (120) in handle (110), the distal end of transducer module (120) is angled downwardly toward cavity (250) of handle (110). Waveguide (320) is then inserted into the cavity (250) and coupled with shaft assembly (170). The electronics module (360) is aligned with and slotted in gap (230) formed by lever ends (210, 220). The proximal end of transducer module (120) is then inserted into cavity (250) of handle (110). Once transducer module (120) has been seated onto handle (110), the two components may be secured together with one or more of the fastening features as detailed above. Of course, the order and positioning may take any other suitable steps. Once transducer module (120) is installed in handle (110) to form assembled surgical device (100), toggle button (140) is operable to actuate mechanical lever end (210), which in turn actuates first button (340) of electronics module (360). The trigger assembly (130) is operable to actuate mechanical lever end (220), which in turn actuates second button (390) of electronics module (360).

In the present example, first button (340) is operable to selectively activate transducer module (120) and harmonic blade (174). For instance, transducer module (120) and harmonic blade (174) may remain activated for so long as first button (340) is depressed, with transducer module (120) and harmonic blade (174) being deactivated as soon as first button (340) is released. As another merely illustrative example, transducer module (120) and harmonic blade (174) are activated and remain activated when first button (340) is clicked (e.g., pressed and released) once; then are deactivated when first button (340) is clicked again. Other suitable relationships between first button (340) and activation of transducer module (120) and harmonic blade (174) will be apparent to those of ordinary skill in the art in view of the teachings herein.

Continuing with the present example, second button (390) is operable to selectively toggle transducer module (120) between a maximum power level mode and a minimum power level mode. As another merely illustrative example, a button of electronics module (360) may be operable to power a motor, solenoid, or other feature to selectively pivot clamping member (176). Alternatively, a separate trigger feature of handle (110) may be operable to provide selective pivoting of clamping member (176). For instance, as noted above, trigger (130) and tab (1226) of FIG. 7 may provide selective pivoting of clamping member (176), without requiring either button (340, 390) to be depressed in order for clamping member (176) to pivot. As yet another merely illustrative example, surgical device (100) may require simultaneous actuation of button (140) and trigger (130), or one or both of buttons (1141, 1142) and trigger (130), in order for blade (174) to be activated. By way of example only, button (1141) may provide minimum power while button (1142) may provide maximum power. The user may select the desired power level by holding the appropriate button (1141, 1142), then actuate trigger (130) while still holding the selected button (1141, 1142). Blade (174) may activate at the selected power level as soon as trigger (130) is actuated. Other suitable operabilities and relationships between components will be apparent to those of ordinary skill in the art in view of the teachings herein.

Electronics module (360) of the present example is further provided with an over-molded boot (330) as depicted in FIGS. 3-4. Transducer module (120) includes a groove or a lip (360) for securing the over-molded boot (330) to prevent fluids and/or contaminants from reaching electronics module (360). In some versions, over-molded boot (330) may be removably attached to transducer module (120). Alternatively, over-molded boot (330) may be permanently attached to transducer module (120). As another merely illustrative example, buttons (340, 390) may be replaced with reed switches, and lever ends (210, 220) may include integral magnets that are operable to selectively activate the reed switches upon reaching sufficient proximity with the reed switches. In some such versions, boot (330) is simply eliminated. Furthermore, the entire transducer module (120) may be provided within an entirely sealed housing in some such versions, with only waveguide (320) being exposed relative to the housing. Other suitable configurations will be apparent to those of ordinary skill in the art in view of the teachings herein.

In some versions, transducer module (120) may be provided with a seal or gasket (not shown) along or adjacent to a mating edge (370) of transducer module (120) for engaging the outer lip (254) defining cavity (250) of handle (110). This seal or gasket may be provided to further prevent liquids or contaminants from entering surgical device (100) once transducer module (120) is installed in handle (110).

Figure 6:
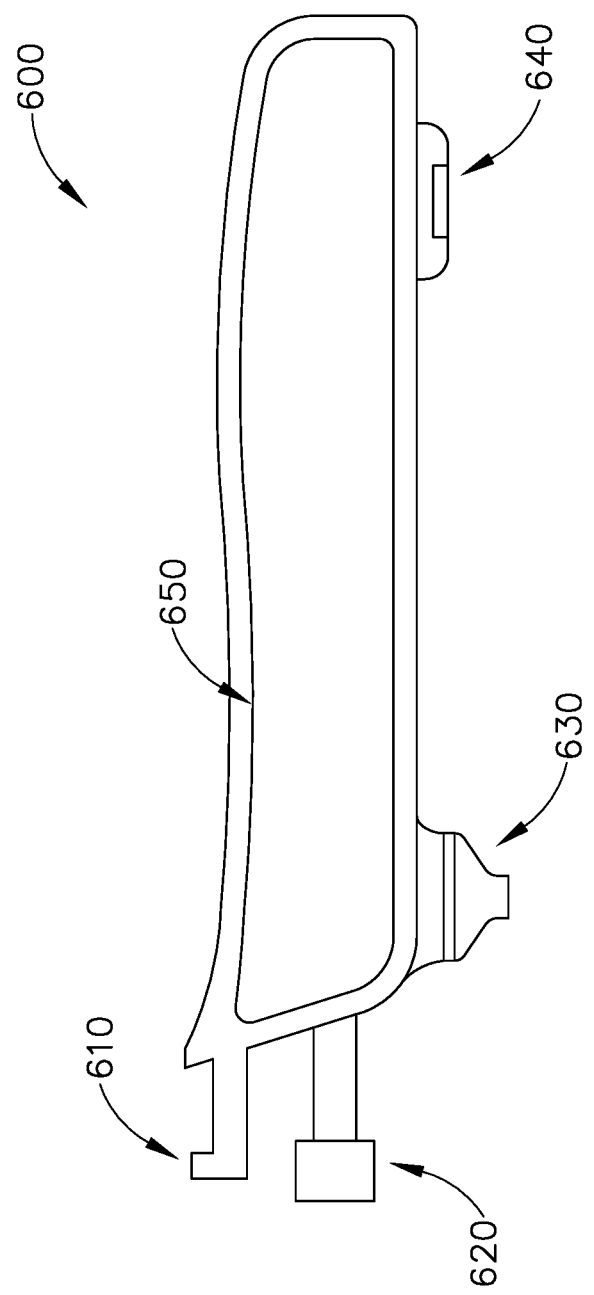
FIG. 6 depicts a side elevation view of an exemplary alternative removable transducer module, with a connection module.

As noted above, transducer module (120) of the present example includes an integral cable (410), which is accommodated by recessed edge (240) of handle (110) when transducer module (120) is seated in handle (110). FIG. 6 depicts a side elevation view of an exemplary alternative removable transducer module (600) that may be used with handle (110) as described above. Like transducer module (120) described above, transducer module (600) also comprises a tab hook (610), a waveguide (620), an electronics module (630), and a mating edge (650). Transducer module (600) of this example further comprises a connection interface (640). In versions where generator (150) and/or power source (160) are provided within the handle or are connected directly to handle (110) via a cable, connection interface (640) provides transducer module (600) with an electrical coupling with generator (150) and/or power source (160) within handle (110). In particular, connection interface (640) is configured to mate with a complementary connection interface (not shown) in handle (110) when transducer module (600) is seated in handle (110). Connection interface (640) may take the form of electrical contacts, capacitive plates, inductive coils, etc. Of course, connection interface (640) may take any other suitable form.

Electronics module (630) of transducer module (600) may further include a plurality of buttons (not shown). For instance, a button may be provided to power on and off the surgical device (100). As another merely illustrative example, a plurality of buttons may be provided on transducer module (600) to adjust the power level and/or frequency level of surgical device (100). Such buttons need not necessarily be provided as part of electronics module (630), and may instead be positioned in locations such as those where a user may directly actuate the buttons after transducer module (600) is seated in handle (110). Such buttons may also be provided on handle (110), if desired. Still other input configurations for transducer module (600) will be apparent to those of ordinary skill in the art in view of the teachings herein.

It is contemplated that various teachings herein may be combined in numerous ways, and it should be understood that none of the teachings herein are intended to represent the limits of the inventors' contemplation. Various other examples of how several features of the surgical device (100) may be carried out in practice will be apparent to those of ordinary skill in the art in view of the teachings herein, and those examples are well within the inventors' contemplation.

Further by way of example only, at least a portion of surgical device (100) may be constructed in accordance with at least some of the teachings of U.S. Pat. No. 6,500,176 entitled "Electrosurgical Systems and Techniques for Sealing Tissue," published Dec. 31, 2002, the disclosure of which is incorporated by reference herein; U.S. Pat. No. 7,416,101 entitled "Motor-driven Surgical Cutting and Fastening Instrument with Loading Force Feedback," published Aug. 26, 2008, the disclosure of which is incorporated by reference herein; U.S. Pat. No. 7,738,971 entitled "Post-sterilization Programming of Surgical Instruments," published Jun. 15, 2010, the disclosure of which is incorporated by reference herein; U.S. Pub. No. 2006/0079874 entitled "Tissue Pad for Use with an Ultrasonic Surgical Instrument," published Oct. 7, 2005, the disclosure of which is incorporated by reference herein; U.S. Pub. No. 2007/0191713 entitled "Ultrasonic Device for Cutting and Coagulating," published Oct. 11, 2006, the disclosure of which is incorporated by reference herein; U.S. Pub. No. 2007/0282333 entitled "Ultrasonic Waveguide and Blade," published May 22, 2007, the disclosure of which is incorporated by reference herein; U.S. Pub. No. 2008/0200940 entitled "Ultrasonic Device for Cutting and Coagulating," published Jan. 15, 2008, the disclosure of which is incorporated by reference herein; U.S. Pub. No. 2009/0209990 entitled "Motorized Surgical Cutting and Fastening Instrument Having Handle Based Power Source," published Feb. 14, 2008, now U.S. Pat. No. 8,657,174, issued Feb. 25, 2014, the disclosure of which is incorporated by reference herein; U.S. Pub. No. 2010/0069940 entitled "Ultrasonic Device for Fingertip Control," published Sep. 11, 2009, now U.S. Pat. No. 9,023,071, issued May 5, 2015, the disclosure of which is incorporated by reference herein; U.S. Patent App. Publ. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery systems is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical device, comprising:
   (a) a detachable module comprising a transducer operable to convert electrical power into ultrasonic vibrations, wherein the detachable module further comprises an electronics assembly, wherein the electronics assembly comprises at least one button, wherein the at least one button is configured to actuate to thereby cause the transducer to convert electrical power into a at least one corresponding level of ultrasonic vibrations;
   (b) a body, comprising:
      (i) a housing having a distal end and a proximal end, wherein the housing is configured to removably receive the detachable module,
      (ii) a shaft assembly extending distally from the distal end of the housing, and
      (iii) a trigger assembly movably coupled with the housing, wherein the trigger assembly comprises at least one lever member, wherein the at least one lever member is operable to directly engage a corresponding button of the at least one button so as to selectively activate the transducer at an associated level of ultrasonic vibrations; and
   (c) a locking feature operable to selectively secure the detachable module to the body.

2. The surgical device of claim 1, wherein the electronics assembly is operable to adjust a power level of the transducer.

3. The surgical device of claim 1, wherein the locking feature comprises a hooked tab extending integrally from the detachable module.

4. The surgical device of claim 1, wherein the detachable module comprises a waveguide extending distally from the detachable module.

5. The surgical device of claim 1, wherein the detachable module comprises a cable extending proximally from the detachable module.

6. The surgical device of claim 1, wherein the detachable module comprises a connection interface disposed on an underside of the detachable module, wherein the connection interface is configured to provide electrical communication between the detachable module and the body.

7. The surgical device of claim 1, wherein the detachable module comprises a lower edge sealingly engaged with the housing.

8. The surgical device of claim 1, wherein the detachable module and the body together form a substantially flush surface.

9. The surgical device of claim 1, wherein the electronics assembly further comprises:
   a base portion, and
   (ii) a switch member including the first button and the second button.

10. The surgical device of claim 9, wherein the base portion further comprises a lip portion disposed along a perimeter of the base portion, the electronics assembly further comprising an overmolded boot portion secured to the lip portion.

11. The surgical device of claim 9, wherein the switch member extends perpendicularly from the base portion and the first button and the second button are disposed on a lateral surface of the switch member.

12. A surgical device, comprising:
   (a) a detachable transducer module, the detachable transducer module comprising:
      (i) one or more piezoelectric elements operable to convert electrical power into ultrasonic vibrations, and
      (ii) a switch assembly in communication with the one or more piezoelectric elements, wherein the switch assembly comprises at least one button, wherein the at least one button is operable to selectively activate the one or more piezoelectric elements,
      wherein the transducer module is operable to selectively toggle the one or more piezoelectric elements between a first power level and a second power level, wherein the first power level is different from the second power level;
   (b) a housing having a distal end and a proximal end, wherein the housing is configured to selectively engage the detachable transducer module;
   (c) a shaft assembly extending distally from the distal end of the housing, wherein at least part of the shaft assembly is configured to receive ultrasonic vibrations communicated from the detachable transducer module; and (d) a trigger assembly movably coupled with the housing, wherein a portion of the trigger assembly is operable to selectively directly contact the switch assembly when the detachable transducer module is engaged with the housing to thereby activate the one or more piezoelectric elements.

13. The surgical device of claim 12, wherein at least part of the switch assembly is exposed, wherein the exposed part of the switch assembly comprises a flexible boot, wherein the flexible boot covers the first button and the second button.

14. The surgical device of claim 12, wherein the shaft assembly comprises an end effector having a clamp arm.

15. The surgical device of claim 14, wherein the trigger assembly comprises a clamp actuating tab fixed to a portion of the shaft assembly, wherein the clamp actuating tab is operable to actuate the clamp arm of the end effector.

16. The surgical device of claim 15, wherein the trigger assembly further includes a lever member, wherein the lever member is operable to selectively directly contact the switch assembly, wherein the lever member is fixed to the clamp actuating tab.

17. A surgical device, comprising:
(a) a detachable module comprising:
  (i) a transducer operable to convert electrical power into ultrasonic vibrations, and
  (ii) an electronics assembly extending from the transducer, wherein the electronics assembly comprises a first button and a second button, wherein the first button is configured to actuate to thereby cause the transducer to convert electrical power into ultrasonic vibrations, wherein the second button is configured to provide at least a first energy level of ultrasonic vibrations; and
(b) a body, comprising:
  (i) a housing, wherein the housing is configured to removably receive the detachable module,
  (ii) a shaft assembly extending distally from the housing, and
  (iii) a trigger assembly movably coupled with the housing, wherein the trigger assembly comprises a first trigger and a second trigger, wherein the first trigger comprises a first lever member operable to make direct contact with the first button, wherein the second trigger comprises a second lever member operable to make direct contact with the second button.

18. The surgical device of claim 17, wherein the first lever member and the second lever member define a gap, wherein the electronics assembly extends from the transducer into the gap.

19. The surgical device of claim 17, wherein the electronics assembly further comprises a third button configured to provide a second energy level of ultrasonic vibrations.

20. The surgical device of claim 19, wherein the trigger assembly comprises a third trigger, wherein the third trigger comprises a third lever member operable to make direct contact with the third button.

* * * * *